United States Patent [19]
Hickmann et al.

[11] 4,087,867
[45] May 9, 1978

[54] OPHTHALMIC PROSTHESIS IMPLANT

[75] Inventors: Horst R. Hickmann, Cincinnati, Ohio; Roosevelt A. Albert, Auburn, Ala.

[73] Assignee: Horst R. Hickmann, Cincinnati, Ohio

[21] Appl. No.: 711,884

[22] Filed: Aug. 5, 1976

[51] Int. Cl.² ............................................. A61F 1/16
[52] U.S. Cl. .......................................................... 3/13
[58] Field of Search ......................................... 3/13, 1

[56] References Cited
U.S. PATENT DOCUMENTS

| | | | |
|---|---|---|---|
| 2,571,721 | 10/1951 | Jardon | 3/13 |
| 2,660,732 | 12/1953 | Stone | 3/13 |

*Primary Examiner*—Ronald L. Frinks
*Attorney, Agent, or Firm*—Melville, Strasser, Foster & Hoffman

[57] ABSTRACT

An ophthalmic prosthesis implant to be used as a replacement and cosmetic correction for the loss of an eye due to injury or illness and to fill the orbital cavity formally occupied by the natural eye. The implant includes a generally hemispherical cartridge member having pins protruding therefrom for affixing and permanently attaching the member to the skeletal skull, and an eye prosthesis removably secured to the cartridge member.

A pliers like instrument is disclosed for applying the cartridge member, along with an eye prosthesis applier and a periorbital retractor.

8 Claims, 23 Drawing Figures

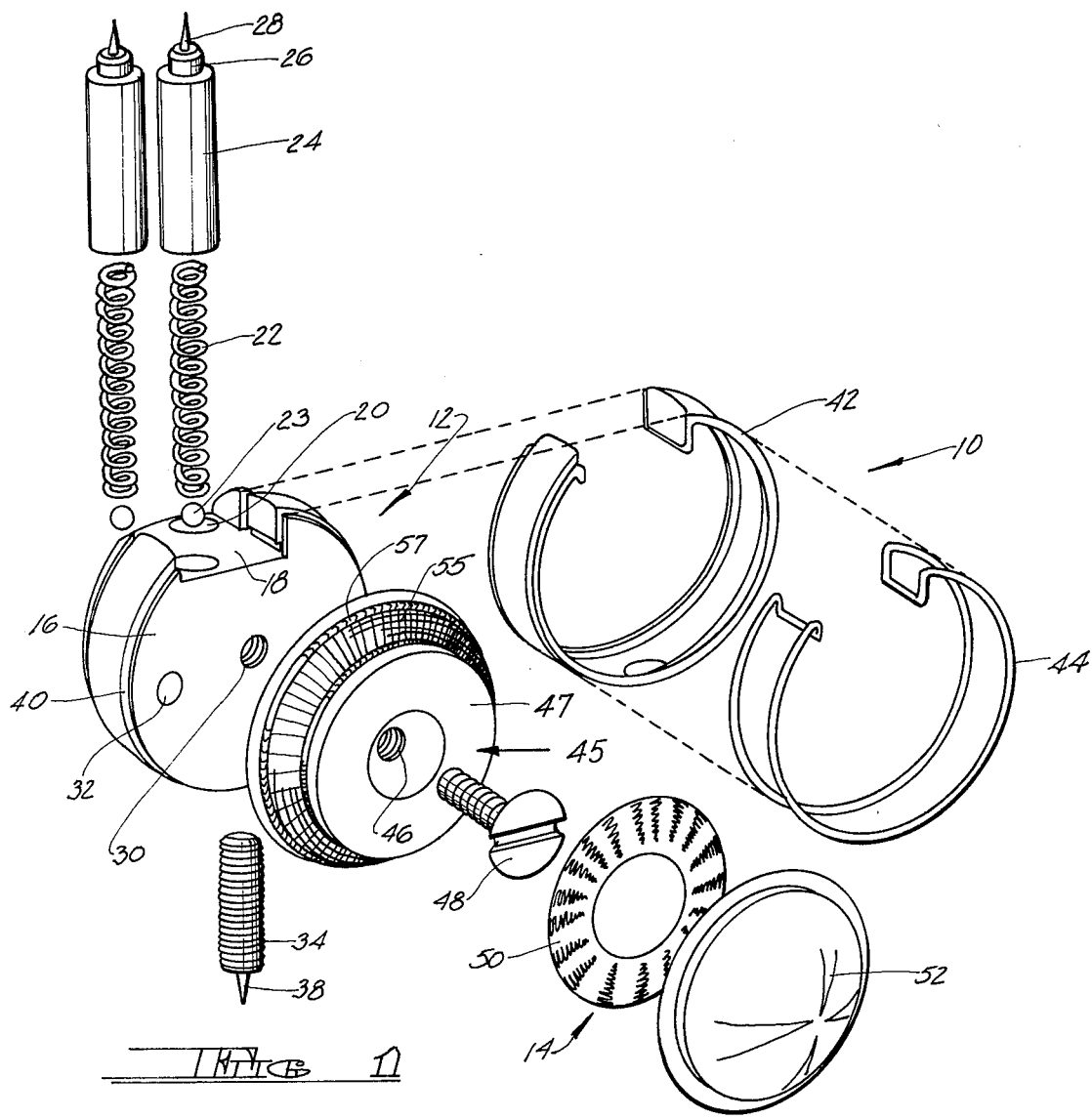
FIG. 1
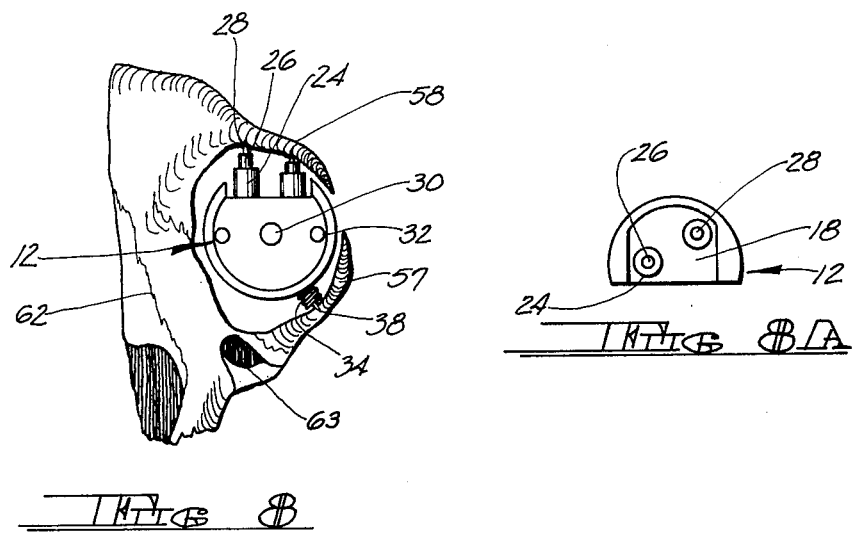
FIG. 8
FIG. 8A

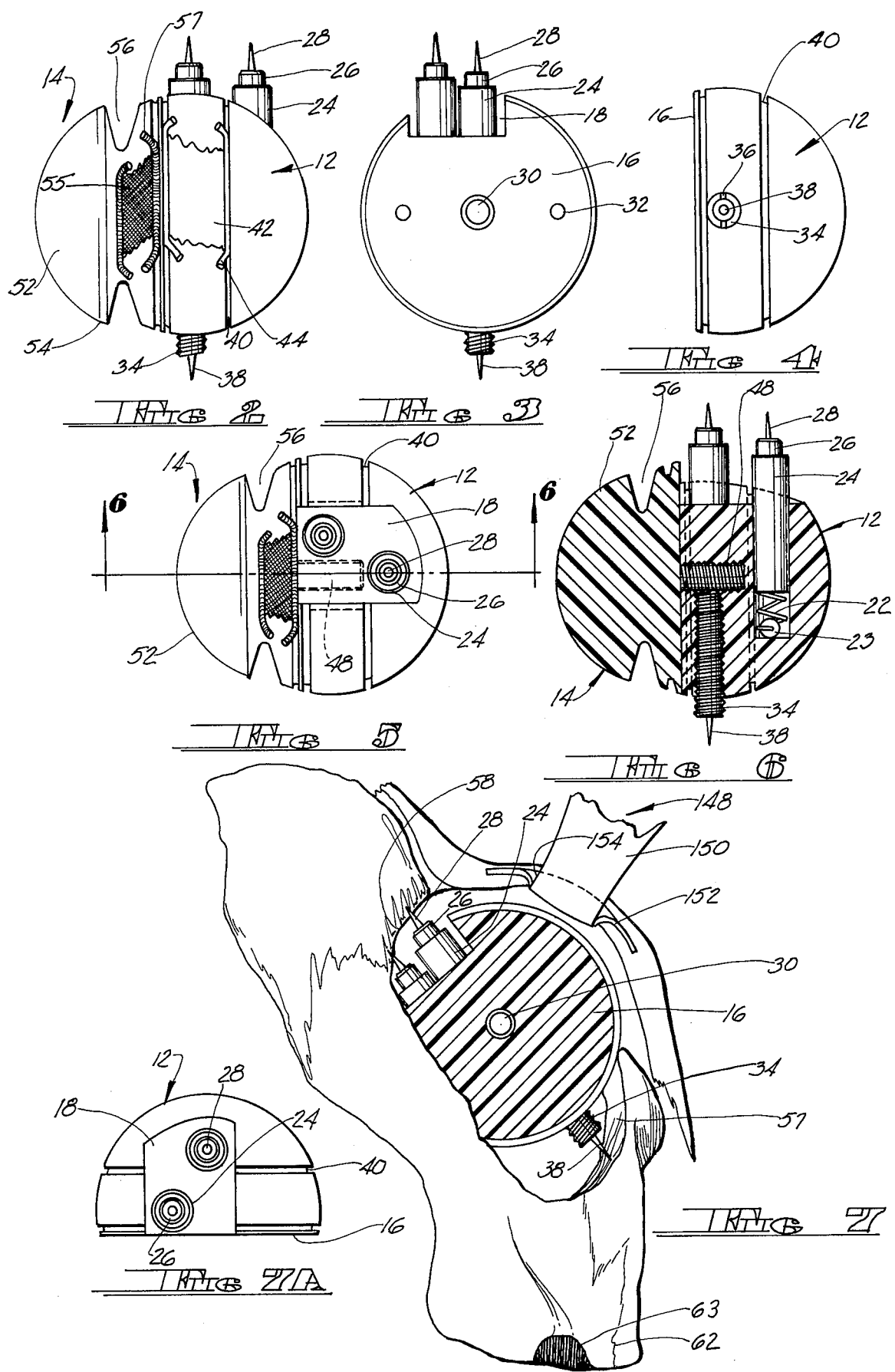

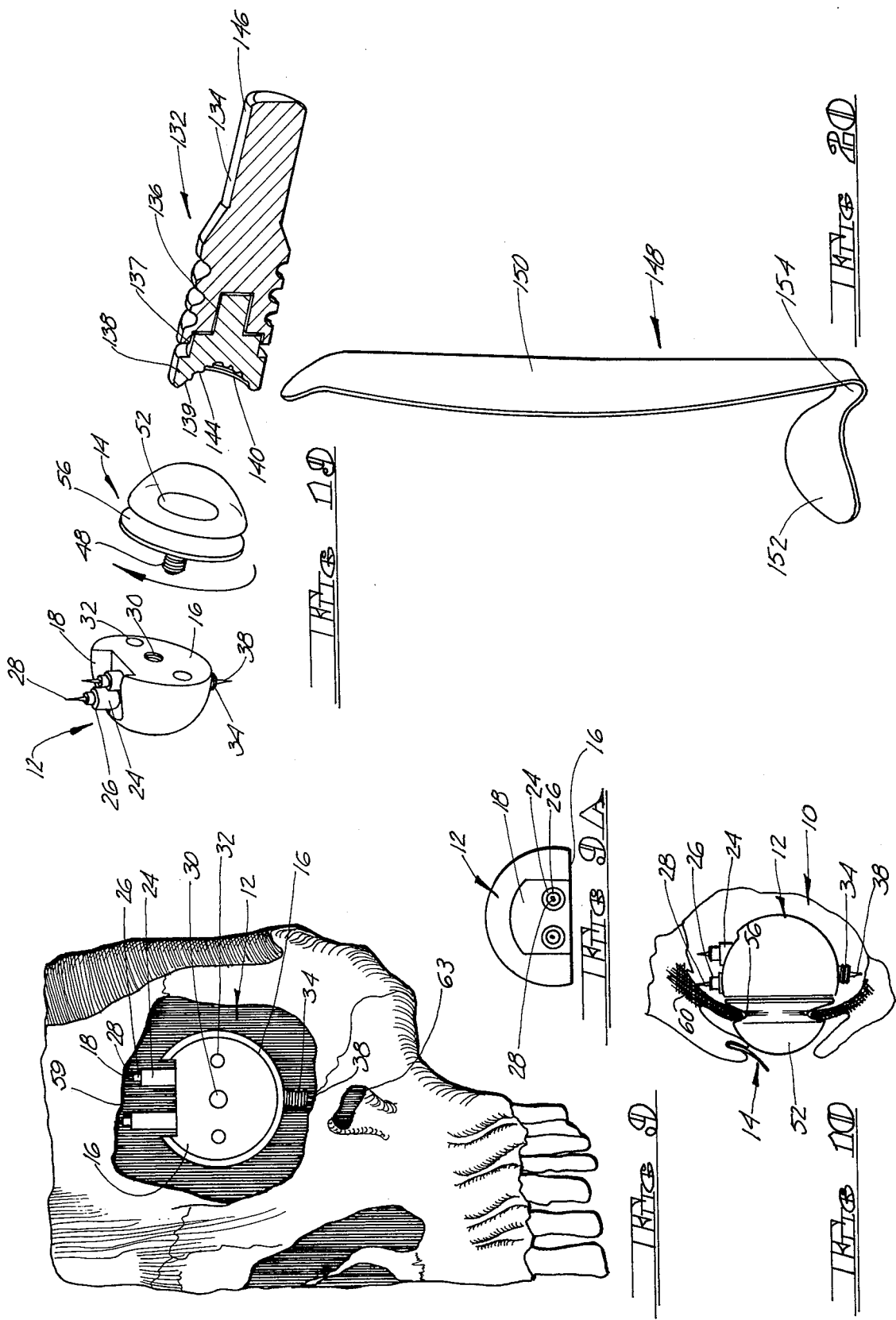

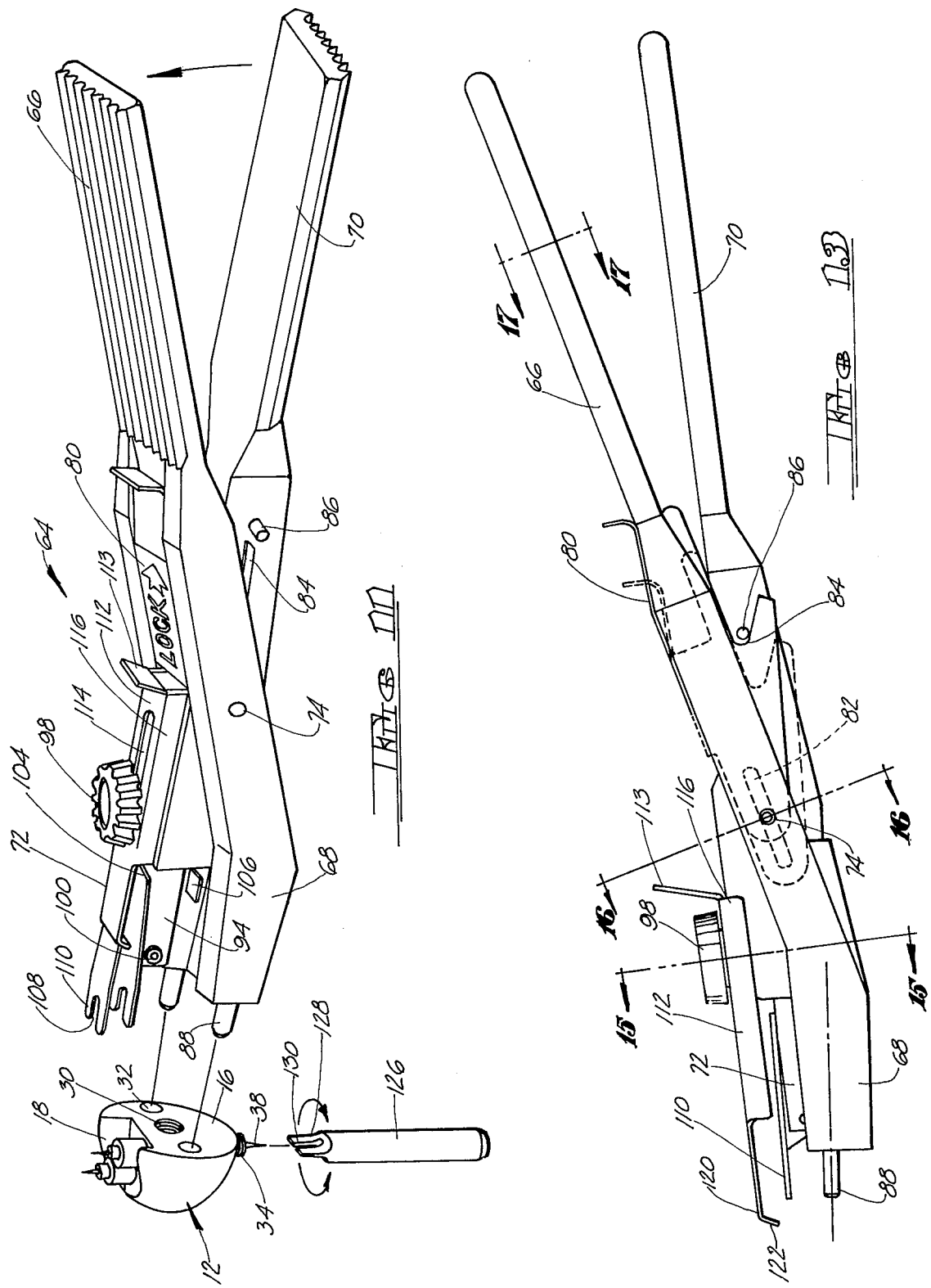

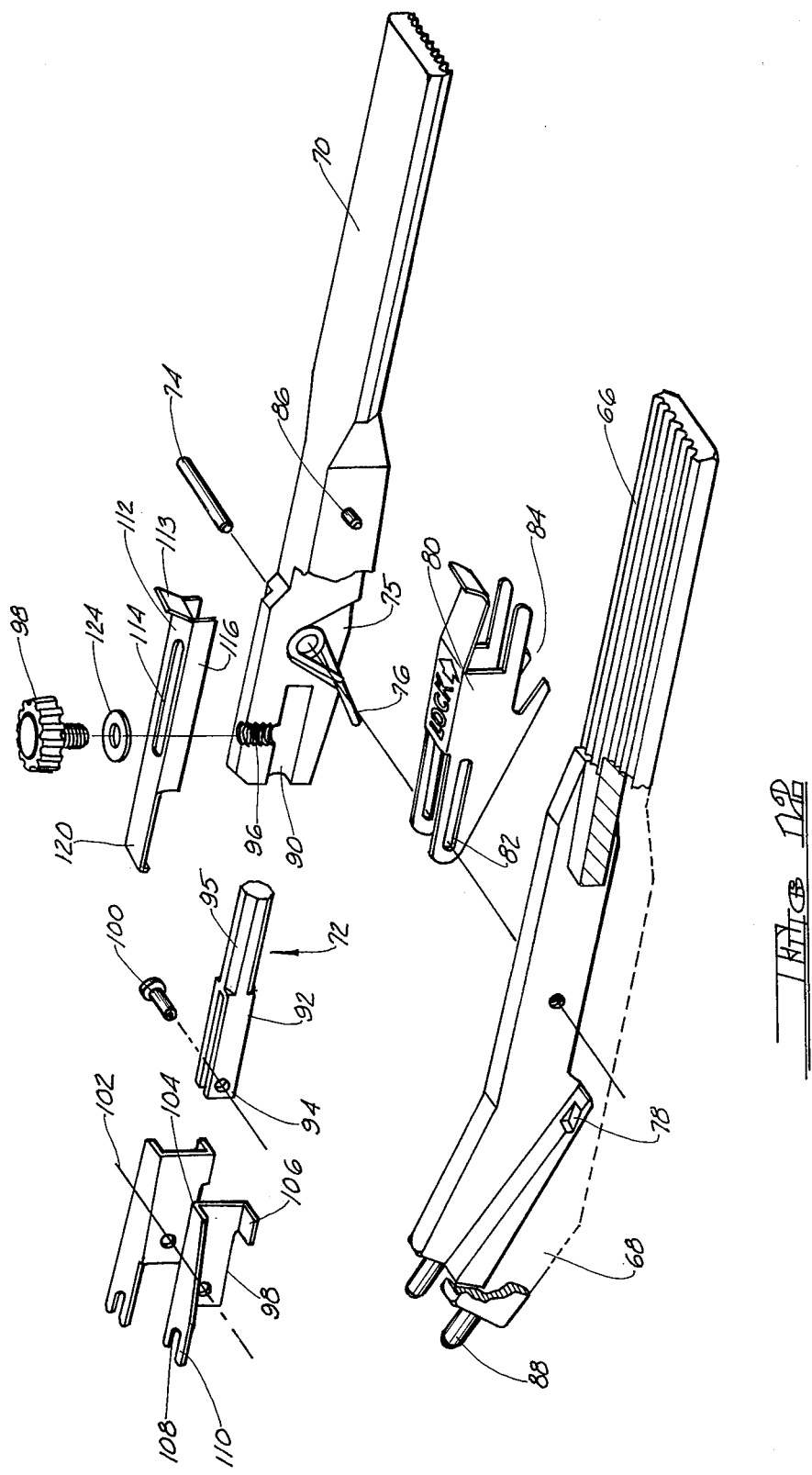

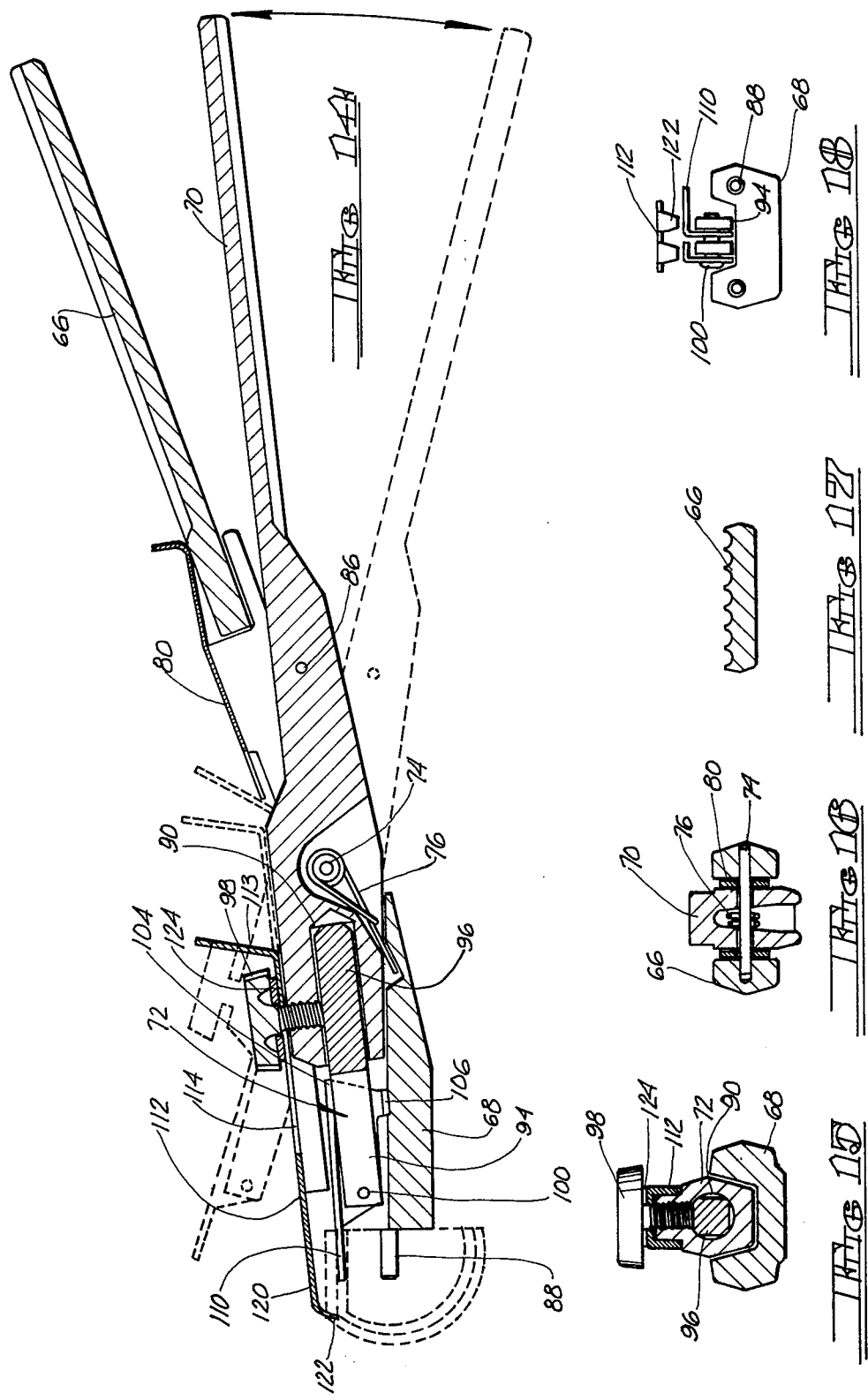

OPHTHALMIC PROSTHESIS IMPLANT

BACKGROUND OF THE INVENTION

1. Field of the Invention

The invention relates to improvements in artificial eyes of the type known as "implants" which are used as replacements for natural eyes when the latter have been enucleated. The invention involves both a novel implant structure and also a new method of making and using such structure. Additionally, the invention involves various instruments for placing the implant eye prosthesis.

2. Description of the Prior Art

While this art has long been practiced, present procedure is such that after enucleation of the globe, a sphere is inserted into the orbital cavity and the conjunctiva is surgically closed over the sphere. A glass shell is then placed on top of this sutured area. The glass shell is held in place by the eyelids. The shells should be removed each night for safety and sanitary reasons.

SUMMARY OF THE INVENTION

The present invention provides an ophthalmic prosthesis implant to be used as a replacement and cosmetic correction for the loss of an eye due to injury or illness and to fill the orbital cavity formally occupied by the natural eye. In its broadest application, the implant includes a generally hemispherical cartridge member having pins protruding therefrom, for affixing and permanently attaching the member to the orbital portion of the skull, and an eye prosthesis removably secured to the cartridge member. At least one of the pins is stationary and two of the pins are compressible such that they may be retracted beneath the surface of the member. After enucleation of the globe, the cartridge member is placed into the orbital cavity and secured by the stationary pin penetrating the periosteum and cortical bone of the inferior orbit or zygomatic bone and the two compressible pins penetrate the periosteum and cortical bone of the superior portion of the orbit. The prosthesis is then screwed into the cartridge and the conjunctiva is drawn into a groove located directly behind the iris by means of a pursestring suture. This places the severed edge of the conjuctiva near its natural position.

This type of cosmetic replacement might be desirable for the mentally incompetent, older persons with physical short comings and animals such as canines and felines. By making frequent removal impossible or unnecessary it, will also replace the present system.

The present invention also provides a pliers like instrument for applying the opthalmic prosthesis implant. The instrument includes an upper handle terminating in a lower jaw and a lower handle provided with a removable upper jaw. The handles are pivoted together behind the jaws thereof and are shiftable between an open position, wherein the jaws are spaced, and a closed position, wherein the jaws approach each other for the engagement of a cartridge member therebetween. Means are provided to bias the handles to the open position. The lower jaw is provided with protruberances extending therefrom to mate with associated bores within the cartridge member. The removable upper jaw is provided with bifurcated claw like tip members which mate with the protruding pins of the cartridge member. When the jaws are in the open position, the protruberances of the lower jaws are received within the mating bores of the cartridge member and the bifurcated tip members of the upper jaw are associated with the protruding pins of the cartridge members. When the jaws are shiftable to the closed position, the pins are retracted below the spherical surface of the cartridge member, preparatory to placing the implant in the orbital cavity, and then released when the implant is positioned as desired in the orbital cavity, so that the implant is affixed and permanently attached to the orbital portion of the skull by means of the pins.

The present invention also contemplates an eye prosthesis applier. The applier includes an elongated base member having an aperture at one end thereof and a suction cup member having a concave cavity and a cylindrical stub protruding from the exterior of said cavity for mating with the aperture in the base member.

The present invention also includes a periorbital retractor comprising a curved concave handle and an inverted spoon shaped portion protruding backward and substantially perpendicular to the handle from one end thereof.

BRIEF DESCRIPTION OF THE DRAWING

FIG. 1 is an exploded view showing the opthalmic prosthesis implant of the present invention.

FIG. 2 is a side elevation of the opthalmic prosthesis implant.

FIG. 3 is a front elevation of the cartridge member.

FIG. 4 is a bottom elevation of the cartridge member.

FIG. 5 is a plan view of the opthalmic prosthesis implant.

FIG. 6 is a cross sectional view taken on the line 6—6 of FIG. 5.

FIG. 7 discloses a front elevational view showing the cartridge member as positioned in the left orbital cavity of a medium sized canine and also showing a portion of the periorbital retractor.

FIG. 7A is a plan view of the cartridge member of FIG. 7.

FIG. 8 is a front elevation showing the cartridge member of the opthalmic prosthesis implant of the present invention as positioned in a feline.

FIG. 8A is a top plan view of the cartridge member of FIG. 8.

FIG. 9 is a front elevation showing the cartridge member of the opthalmic prosthesis implant of the present invention as positioned in a human.

FIG. 9A is a plan view of the cartridge member of FIG. 9.

FIG. 10 is a side elevation showing the opthalmic prosthesis implant of the present invention and more particularly how the severed edge of the conjunctiva is drawn into a suture groove located behind the cornea by a pursestring suture.

FIG. 11 is a perspective view showing the cartridge member applier of the present invention along with the adjustment instrument and cartridge member.

FIG. 12 is an exploded perspective view of the cartridge applier of FIG. 11.

FIG. 13 is a side elevation of the cartridge applier.

FIG. 14 is a center line cross sectional view through the cartridge applier.

FIG. 15 is a cross sectional view taken on the line 15—15 of FIG. 13.

FIG. 16 is a cross sectional view taken on the line 16—16 of FIG. 13.

FIG. 17 is a cross sectional view taken on the line 17—17 of FIG. 13.

FIG. 18 is a partial front elevation of the cartridge applier of FIG. 13.

FIG. 19 is a perspective view, partially in cross section, of the prosthesis applier of the present invention.

FIG. 20 is a perspective view of the periorbital retractor of the present invention.

DESCRIPTION OF THE PREFERRED EMBODIMENTS

FIGS. 1 through 6 best disclose the ophthalmic prosthesis implant 10 of the present invention. As will be more fully explained hereinafter, the implant 10 of the present invention is to used as a replacement and cosmetic correction for the loss of an eye due to injury or illness and to fill the space formally occupied by the natural eye.

As can be seen, the opthalmic prosthesis implant 10 includes the cartridge member 12 and an eye prosthesis 14 removably secured to the cartridge member 12. The cartridge member 12 is a generally hemispherical member having a flat side 16. A recess 18 is provided in the member 12. Two parallel bores 20 with steel liners receive the compression springs 22 and the pistons 24. Additional extension of the springs 22 is necessary in some instances and the ball 23 may be placed in the bores 20. Each piston 24 has a smaller cylindrical boss 26 at the top thereof. Positioned on the boss 26 is a pointed pin 28. The bores 20 in the recess 18 permit compression of the pistons 24, and thus the retraction of the points of the pins 28 below the spherical circumference of the cartridge member 12.

The flat side or large circular flat plane 16 of the cartridge member 12 is provided with a threaded bore 30 in the center thereof and with two plan bores 32, one to each side of the threaded bore 30. Parallel to the pistons 24, but protruding at the opposite side of the cartridge member 12, is a threaded screw 34. The threaded screw 34 is provided with a transverse slot 36 at one end and a sharply pointed pin 38 protrudes from the center of the slot 36.

Two parallel grooves 40 extend circumferentially around the equator or center of the cartridge member 12. The grooves 40 receive a synthetic fabric 42, which is held in place by a synthetic thread 44. For purposes of clarity, the synthetic fabric 42 and the synthetic thread 44 are omitted from most of the other figures.

The eye prosthesis 14 comprises a base 45 having through its center a threaded hole 46 with a counter bore to receive a flat head machine screw 48. The protruding threaded shaft of the screw 48 fastens the eye prosthesis 14 to the cartridge member 12 by mating with the threaded bore 30. A facsimile of the iris 50 is produced by lithographic or photographic process and placed onto the surface 47 of the base 45 and covered with the cornea 52. A chemical weld at the rim 54 produces an air and water tight encapsulation of the iris 50. A suture groove 56 is located behind the cornea 50 of the eye prosthesis 14. A synthetic fabric 55 is held in place by a synthetic thread 57 to the rearmost surface of the suture groove 56.

The method of applying the ophthalmic prosthesis implant 10 of the present invention will more fully be explained hereinafter following an explanation of the various instruments used therewith. However, it should be emphasized that the cartridge member 12 of the implant 10 is affixed and permanently attached to the orbital portion of the skull by means of a three point one axis fixation accomplished by the use of the adjustable pin 38 and the two spring loaded pistons 24, each having a pin 28 at its outermost end. The pins 28 and 38 embed themselves in the orbital bone. The eye prosthesis 14 is affixed to the cartridge member 12 by being screwed into the cartridge member 12. The cartridge member 12 and the eye prosthesis 14 replace the cavity formally occupied by the natural eye.

The space between the ophthalmic prosthesis implant 10 i.e., the cartridge member 12 and the eye prosthesis 14, and the orbital bone is occupied by the periorbital fat, extra ocular muscles, vessels, nerves and granular tissues. The pins 28 and 38, which include the adjustable pin 38 and the anterior and posterior pistons 24 with the pins 28 at their extreme ends, penetrate the periorbital fat and embed themselves in the orbital bone.

In practice, the pins 28 and 38 will embed themselves into the outer bone table of the orbital skull. In each species including man, the placement of the pins 28 and 38 will vary. The stationary pin 38 will carry the same load or pressure as the two pins 28 located at the ends of the pistons 24. Since there are two pins 28 on the pistons 24, each will bear only half the load of that pin 38 on the stationary screw 34. For this reason, the stationary pin 38 must be placed in the most solid bone or heaviest outer bone table. For example, in the canine example of FIG. 7, the stationary pin 38 is placed in the dorsal aspect of the zygomatic arch 57, which is a slightly tilted plane measuring about 2–3 mm width. The pins 28 located at the end of the pistons 24 are positioned into the anterior edge 58 of the orbital process of the frontal bone which is the supraorbital margin containing the frontal sinus.

The pins 28 and 38 will seat themselves in the periosteum and over a period of several weeks will penetrate the cortical bone until a complete integrity between bone and implant 10 are achieved and the springs 22 are retired.

A secondary attachment is obtained by the severed tissues within the orbital cavity growing into the synthetic fabric 42 affixed to the cartridge member 12. This heals the severed tissues which were formally attached to the natural eye.

A third attachment is obtained when the severed edge of the conjunctiva 60, as best seen in FIG. 10, is drawn into the suture groove 56 by means of a purse string suture. Thus, instead of merging or blending into the area around the cornea 52, the conjunctiva is now mechanically closed immediately behind the cornea 52.

A fourth attachment is obtained when the subconjunctival of the confunctiva tissue 60, as best seen in FIG. 10, grows into the synthetic fabric, 55 on the rearmost surface of the suture groove 56, which is held in place by a synthetic thread 57, thereby reinforcing the newly created aperature and preventing breakdown of the conjunctiva 60.

It will, of course, be noted that the total volume replacement of the ophthalmic prosthesis implant 10 into the orbital cavity will prevent deformation of the outer skin line of the patient, especially the species canine which does not have a completely orbital rim. Ligaments closing this gap would collapse if the total volume replacement was absent.

FIGS. 7, 8 and 9 show the left orbit in canine, feline and human skulls with the cartridge member 12 of the ophthalmic prosthesis implant 10 in position. The two pistons 24 place their pins 28 in the supraorbital bone 59 in humans and in the frontal bone 58 in canines (FIG. 7) and felines (FIG. 8). The infraorbital foramen 63 is shown as a reference point common to all three species. The suture lines 62 are not to be confused with surgical sutures but are also common to all three types of skulls shown. FIGS. 7A, 8A and 9A are plan views of each size cartridge member 12 used for canine, feline and human skulls. Only the canines require all three sizes shown, while humans would utilize 24.0 mm and felines 19.0 mm cartridge members 12.

An instrument 64 for applying an ophthalmic prosthesis implant 10 of the present invention is shown in FIGS. 11 through 18. The instrument 64 includes an upper handle 66 terminating in a lower jaw and a lower handle 70 provided with a removable upper jaw 72. The handles 66 and 70 are pivoted together at the pin 74 behind the jaws 68 and 72 thereof and are shiftable between an open position, wherein the jaws 68 and 72 are spaced, and a closed position, wherein the jaws 68 and 72 approach each other for the engagement of a cartridge member 12 therebetween. The handles 66 and 70 are provided with longitudinal serrations. The serrations on the upper handle 66 are on the upper surface, while the serrations on the lower handle 70 are facing downwardly.

A torsion spring 76 is placed about the pin 74 in the recess 75 of the handle 70. The lower jaw 68 of the upper handle 66 is provided with a recess 78 which receives the longer leg 76' of the spring 76. In practice, the spring 76 normally biases the handles 66 and 70 to the open position.

As can be seen, a locking member 80 slides on the handles 66 and 70. The locking member 80 is generally U-shaped so that it will slide with the handles 66 and 70 between the bifurcations thereof. The forwardly most end of the locking member 80 is provided with spaced parallel slots 82 which receive the pin 74. The rearwardmost end of the locking member 80 is provided with pin engaging notches 84, which, during operation of the instrument 64, receive or engage the pin 86 protruding from the two outside surfaces of the lower handle 70. Accordingly, as can be seen, when the handles 66 and 70 are shifted to the closed position, wherein the jaws 68 and 72 approach each other for the engagement of a cartridge member 12 therebetween, against the action of the spring 76, the locking member 80 may be moved rearwardly so that the pin engaging notches 84 engage the pin 86, in which case the handles 66 and 70 are maintained in the closed position.

The lower jaw 68 is provided with at least one pin like protruberance 88 extending therefrom to mate with an associated bore 32 in the flat side 16 of the cartridge member 12. The removable upper jaw 72 in the lower handle 70 is received by a longitudinal and horizontal bore 90 in the handle 70. The removable upper jaw 72 comprises an elongated member 92 so configured at one end 96 to be received within the bore 90 and configured at the other end 94 so as to receive the interchangeable tips 94. A threaded bore 96 is provided in the handle 70 substantially perpendicular to and intersecting with the bore 90. The threaded hole 96 receives a torque screw 98, which serves as a fastener for the removable jaw 72. As can be seen, the elongated member or base 92 resembles a tuning fork, with the square and slotted end 94 pointing forwardly and the semisquare and semicircular end 95, which is received in the bore 90 of the handle 70, pointing rearwardly. As previously explained, the portion 95 of the member 92 is received by the bore 90 and the upper surface thereof is contacted by the point of the screw 98. Two claw like tips 98 are attached to the member 92 by means of a rivet 100. The tips may be positioned in the slot in the square and slotted end 94 of the base 92, or one tip may be positioned in the slot and the other outside. The positioning of the claw like tips 98 is determined by the arrangement of the pistons 24 within the cartridge member 12. In all cases, the claw like tips 98 move freely about their axes 102 while the rear edge 104 limits the upward movement of the claw tip 98 and the tab 106 limits the downward movement of the claw tip 98. This produces a necessary floating action. The slot 108 in each tip 98 receives the cylindrical boss 26 of the piston 24 while the bottom surface 110 presses on the surface of the piston 24.

A protective shield 112 having a tab 113, a slot 114 and two parallel flat sides 116, slides in two parallel recesses 118 on the forward end of the handle 70. The slot 114 limits the movement of the shield 112 and the parallel recesses 118 maintain the point 120 of the shield 112 in proper alignment. The point 120 is provided with two tabs 122 which move between the pins 28 on the pistons 24. A curved spring washer 46 keeps the protective shield 112 engaged during its performance by pressing onto the bottom surface of the torque screw 98 and the top surface of the protective shield 112.

As best seen in FIG. 11, an adjustment instrument 126 is provided to adjust the position of the threaded screw 34 in the threaded bore 30 of the cartridge member 12. The adjustment instrument 126 resembles a screw driver with a slot 130 in the blade portion 128. This allows the front edge of the adjustment instrument 126 to engage in the transverse slot 36 of the threaded screw 34 without contacting or damaging the pin 38.

An eye prosthesis applier 132 is shown in FIG. 19. The eye prosthesis applier 132 comprises an elongated base member 134 having an aperture 136 at one end thereof and a suction cup member 138 having a concave cavity 140 and a cylindrical stub 142 protruding from the exterior of the cavity 140 for mating with the aperture 136 in the base member 134. In practice, the suction cup member 138 is provided with annular ridges 144 lining the concave cavity 140 thereof. Additionally, the base member 134 is provided with a knurled cylindrical boss 146.

It has been found that best results are obtained when the suction cup member 138 is made of a soft pliable elastomer and when the suction cup member 138 is affixed to the base member 134 with a silicone base adhesive which fuses the cylindrical stub 142 with the mating aperture 136 in the base member 134.

It should be noted that the aperture 136 is such that the contact point between the base member 134 and the cup 138 prevents additional or accidental movement backward, while the groove 137 permits spreading the flexing of the rim 139 of the cup 138. When the cavity 144 of the suction cup 138 of the applier 132 is pressed onto and about the convex cornea 52 of the eye prosthesis 14, a vacuum type suction will result strengthened by the annular ridges 144 lining the cavity 140 of the suction cup 138. The three annular grooves 148 around the base member 134 are decorative only and serve no function. The knurled end of the base member 134 enables the operator to spin the applier 132 between the thumb and forefinger.

A periorbital retractor 148 is disclosed in FIG. 20. The periorbital retractor 148 includes a curved concave handle portion 150 and an inverted spoon shaped portion 152, which protrudes backwardly and substantially perpendicular from one end of the handle portion 150.

The spoon shaped portion 152 and the handle portion 150 are connected to each other by a semicircular neck portion 154.

The ophthalmic prosthesis implant 10 may be attached to the bony orbit and fill the space formerly occupied by the natural eye by means of an operational procedure now to be described.

It should first be noted that the ophthalmic prosthesis implant 10 and the instruments shown and described herein represent only a portion of the total operative and surgical requirement and that all other instruments and supplies which may be required are not shown or mentioned.

Initially, the surgeon must first ascertain the skull configuration and the size of the skeletal orbit by means of a preoperative radiograph. Following such procedure, the surgeon then utilizes the adjustment instrument 126 to produce the proper projection of the threaded screw 34 and pin 38 to meet the requirement of the recipient orbit.

The cartridge member 12 with its two bores 32 in the flat side 16 is then slid onto the protruding pins 88 of the upper handle 66 of the instrument 64. The locking member 80 is positioned forwardly so that the handles 66 and 70 are in the open or spread apart position. The handles 66 and 70 are then shifted or compressed to the closed position, wherein the jaws 68 and 72 approach each other for the engagement of the cartridge member 12 therebetween. At this time the claw tips 98 with their slots 108 engage the protruding bosses 26 of the pistons 24 until the claw tips 98 come to rest on the surface of the pistons 24. Partial compression of the pistons 24 will be followed by pulling back the lock member 80 until the pin engaging notches 84 contact the pin 86. The protective shield 112 is then moved forwardly by pushing on the tab 113 with the thumb until the point 120 covers the exposed pins 28 of the pistons 24 on the cartridge member 12. This assembly should now be placed on the instrument tray.

The edge 139 of the eye prosthesis applier 132 is then pressed over the convex cornea 52 of the eye prosthesis 14 until the vacuum is established. The sagittal axis of the eye prosthesis 14 should be lined up with the center axis of the eye prosthesis applier 132. This assembly should also be placed on the instrument tray.

After the diseased or damaged natural eye is removed and the surgical area prepared, the surgeon should place a purse string suture in the severed edge of the conjunctive, which formally surrounded the cornea of the natural eye.

The ophthalmic prosthesis implant instrument 64 should then be removed from the instrument tray, the handle 66 and 70 thereof depressed, and the locking member 80 pushed forwardly. When the handles 66 and 70 are totally depressed, the pistons 24 are retracted into their respective bores 20, at which time the cartridge member 12 is inserted into the orbital cavity. The placement for the stationary pin 38 on the threaded screw 34 is determined by an incision exposing, for example, the zygomatic arch 57 or by palpation. When the pin 38 is securely placed, the protective shield 112 is retracted by pulling the tab 113 back until it stops. The pistons 24 are then allowed to expand and, as the first pin 28 is placed, its respective claw tip 98 beings to float until the second pin 28 is seated and its respective claw tip 98 begins to float. The implant instrument 64 is then withdrawn.

The eye prosthesis applier 132, with the eye prosthesis 14 attached thereto, is then utilized to screw the protruding shank of the screw 48 into the central threaded hole 30 in the flat side 16 of the cartridge member 12. When the eye prosthesis 14 contacts the cartridge member 12, the applier 132 is moved outwardly with its edge 139 passing the outer perimeter of the eye prosthesis 14, thereby breaking the vacuum.

The severed edge of the conjunctiva 60 is then drawn into the suture groove 56 by drawing the pursestring suture and tying off the two ends. The orbital cavity is then closed and filled entirely by by opthalmic prosthesis implant 10 with the conjunctiva 60 in its near natural position.

The periorbital retractor 148 is used in order to allow the surgeon maximum visability during work performed within the orbital cavity. It should also be noted that in severing tissues, bleeding might result and necessitate application of a hemostatic clip. or other hemostatic devise. The periorbital retractor 148 will serve well during such unforeseen procedures.

It should, perhaps, be noted that in felines, the two pistons 24 should be placed laterally into the supraorbital margin, as shown in FIG. 8. The stationary screw 34 and its respective pin 38 should be placed into the medial vertical surface of the zygomatic arch 57. In human application, as shown in FIG. 9, the pistons 24 should seat themselves in the supraorbital margin 59 while the stationary pin 38 should be placed directly below in the zygomatic ridge 60.

Although the present invention has been described with a certain degree of particularity, it is understood that the present disclosure has been made by way of example and that changes and details in the structure may be made without departing from the spirit thereof.

We claim:

1. An ophthalmic prosthesis implant to be used as a replacement and cosmetic correction for the loss of an eye due to injury or illness and to fill the space formally occupied by the natural eye, which comprises a generally hemispherical cartridge member, said member having a transverse great circle whose diameter is substantially the same as the natural eye, pins protruding from the outer surface of said cartridge member for affixing and permanently attaching said member to the bony orbit, certain at least of said pins being spring loaded and shiftable between retractable and extended positions and being normally biased to their extended positions, and an eye prosthesis removably secured to said cartridge member.

2. A prosthetic base of the nature of an eye implant comprising a generally hemispherical cartridge member, pins protruding from said cartridge member for affixing and permanently attaching said member to the bony orbit, certain at least of said pins being spring loaded and shiftable between retractable and extended positions and being normally biased to their extended positions, and an eye prosthesis removably secured to said cartridge member.

3. A prosthesis implant for use following ocular enucleation comprising a generally hemispherical cartridge member, pins protruding from said cartridge member for affixing and permanently attaching said member to the bony orbit, certain at least of said pins being spring loaded and shiftable between retractable and extended positions and being normally biased to their extended positions, and an eye prosthesis removably secured to said cartridge member.

4. An opthalmic prosthesis implant to be used as a replacement and cosmetic correction for the loss of an eye due to injury or illness and to fill the space formally occupied by the natural eye, which comprises a generally hemispherical cartridge member having a flat side, said member also having a recess therein, two parallel bores located in said recess, piston means positioned in said bores, each said piston means having a pin protruding from one end thereof, said bores permitting compression of said pistons and retraction of said pins below the spherical surface of said cartridge member, a threaded bore substantially in the center of said flat side, a threaded screw parallel to said piston means and protruding from said cartridge member opposite said recess, said screw being provided at its free end with a pin protruding therefrom, two parallel grooves extending circumferentially around the center of said cartridge member, said grooves having a fabric affixed thereto, and an eye prosthesis removably secured to the flat side of said cartridge member, said eye prosthesis being provided with a suture groove extending therearound, whereby said implant is adapted to be primarily affixed and permanently attached to the bony orbit by means of said pins, a secondary attachment can be obtained by the severed tissues within the orbital cavity growing into said fabric affixed to said cartridge member, and a third attachment can be obtained when the severed edge of the conjunctiva is drawn into said suture groove and secured thereto.

5. The implant according to claim 4, wherein a fabric is affixed to the rearmost surface of said suture groove to provide a fourth attachment for said implant when the subconjunctival tissue grows into said fabric.

6. The implant according to claim 4, wherein each said piston means is provided with a smaller circular boss at the top thereof, said pin extending from said boss.

7. The implant according to claim 4, wherein said threaded screw is provided at one end with a transverse slot and said pin protrudes from the center of said slot.

8. The implant according to claim 4, wherein a threaded bore is provided substantially in the center of said flat side of said cartridge member, and wherein said eye prosthesis comprises a base having through its center a threaded bore, a threaded shaft protruding from said hole to fasten said base to said cartridge member by mating with said threaded bore in said flat side of said cartridge member, a facsimile of the iris secured to said base, said iris being covered by the cornea, said suture groove being positioned behind said cornea.

* * * * *